United States Patent [19]

Wang

[11] Patent Number: 4,888,408

[45] Date of Patent: Dec. 19, 1989

[54] POLYMERIC POLYHYDROXY POLYETHER CONTAINING 1,6-DIAZASPIRO-[4.4]NONANE-2,7-DIONE UNITS

[75] Inventor: Pen C. Wang, Houston, Tex.

[73] Assignee: Shell Oil Company, Houston, Tex.

[21] Appl. No.: 249,934

[22] Filed: Sep. 27, 1988

Related U.S. Application Data

[63] Continuation-in-part of Ser. No. 175,023, Mar. 30, 1988, abandoned.

[51] Int. Cl.$^4$ ..................... C08G 52/26; C08G 69/14
[52] U.S. Cl. ..................................... 528/96; 528/89; 528/97; 528/117; 528/323

[58] Field of Search ................... 528/96, 97, 117, 323

[56] References Cited

U.S. PATENT DOCUMENTS 4,672,102  6/1987  Silvis et al. ........................... 528/97

Primary Examiner—Harold D. Anderson

[57] ABSTRACT

Novel linear polymeric polyhydroxy polyethers characterized by alternating moieties of (1) a 1,6-diaza [4.4] spirodilactam having oxyaryl-containing substituents on each ring nitrogen atom and (2) a 2-hydroxy-1,3-propylene connecting group, exhibit relatively high glass transition temperatures.

14 Claims, No Drawings

POLYMERIC POLYHYDROXY POLYETHER CONTAINING 1,6-DIAZASPIRO-[4.4]NONANE-2,7-DIONE UNITS

RELATED APPLICATION

This application is a continuation-in-part of U.S. patent application Ser. No. 175,023, filed Mar. 30, 1988 now abandoned.

FIELD OF THE INVENTION

This application relates to a linear, polymeric, polyhydroxy polyether incorporating within the polymeric chain a polycyclic structure. More particularly, the invention relates to polymeric, polyhydroxy polyethers incorporating moieties of a 1,6-diaza [4.4] spirodilactam.

BACKGROUND OF THE INVENTION

The term "phenoxy resin" is a generic term used to describe the amorphous, high molecular weight poly(hydroxyethers) derived from reaction of diphenols and epichlorohydrin or the reaction of diphenols with the diglycidyl ether of 2,2-di(4-hydroxyphenyl)propane. The resins are tough, high modulus thermoplastic materials of established commercial utility. For example, a thermoplastic resin marketed by Union Carbide as UCAR Resin ® is produced from epichlorohydrin and 2,2-di(4-hydroxyphenyl)propane. The product of the reaction of 2,2-di(4-hydroxyphenyl)propane and the corresponding diglycidyl ether is a second example of a commerical phenoxy resin. Such resins have established utility in applications such as molded articles, films and packaging materials, coatings and adhesives produced by conventional techniques. The phenoxy resins have not, however, been extensively used as engineering thermoplastics because of relatively low glass transition temperatures.

The reaction product of epichlorohydrin and a spirobiindol is disclosed in U.S. Pat. No. 4,672,102 wherein the products are said to have high heat distortion temperatures. The values reported are from about 131° C. to about 135° C., depending upon the nature of the substituents present The corresponding value for the reaction product of epichlorohydrin and 2,2-di(4-hydroxyphenyl)propane was 88° C. It would be of advantage to provide a class of novel, linear, polycyclic phenoxy-type resins having comparable or even higher glass transition temperatures.

SUMMARY OF THE INVENTION

The present invention provides a class of novel, linear, polyhydroxy polyethers having polycyclic structures within the polymeric chain as well as the novel process for the production thereof. More particularly, the invention relates to polyhydroxy polyethers incorporating alternating moieties of a hydroxy-containing three-carbon bridging group and moieties of a substituted [4.4] spirodilactam having spiro ring nitrogen atoms in the 1- and 6-position.

DESCRIPTION OF THE INVENTION

The novel polyhydroxy polyethers of the invention are linear polymers characterized by alternating moieties of divalent 2-hydroxy-1,3-propylene connecting groups, i.e.,

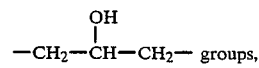

and moieties of a 1,6-diazaspiro[4.4]nonane-2,7-dione compound with oxy-aryl-containing substituents on each spiro ring nitrogen atom. Although polyhydroxy polyethers of a variety of structural modifications are useful for the purposes of the invention, the preferred polyhydroxy polyethers are represented by the repeating formula

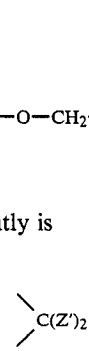 (I)

wherein Z independently is

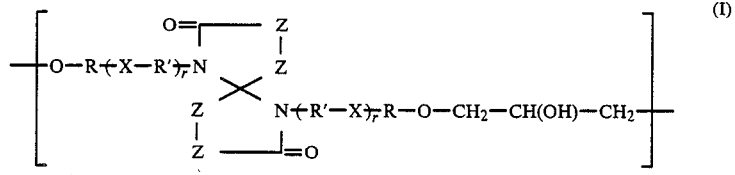

in which Z' independently is hydrogen, lower alkyl of up to 4 carbon atoms inclusive, preferably methyl, or halogen, preferably lower halogens fluoro or chloro, or Z is such that two adjacent Z moieties taken together form a ring system Z' of from ring system Z" of from 5 to 7 ring atoms inclusive, up to two of which are heteroatoms selected from nitrogen, oxygen or sulfur with the remainder of the ring atoms being carbon atoms, there being up to 15 carbon atoms in Z" inclusive, two of which form a connecting bridge between a carbonyl carbon atom, i.e., a carbon atom in the 2- or 7-spiro ring positions, and the spiro carbon atom, i.e., the carbon atom common to the two spiro rings. R in the above formula (I) is aromatic of up to 15 carbon atoms and up to two aromatic rings, inclusive, and R' is R or is aliphatic of up to 10 carbon atoms inclusive. Each of R, R' and Z" is hydrocarbyl except for any heteroatoms in Z", or is substituted hydrocarbyl containing additional atoms such as halogen, preferably the middle halogens chlorine and bromine, present as inert substituents on carbon atoms. The term r in formula (I) independently is 0 or 1 and X independently is a direct valence bond, alkylene of up to 8 carbon atoms inclusive, oxo, thio, sulfonyl, carbonyl, dioxyphenylene, i.e.,

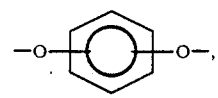

2,2-di(oxyphenyl)propane, i.e.,

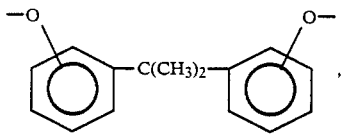

or dioxydiphenylene, i.e.,

The polymeric polyethers of this formula (I) will be further defined in terms of the monomers employed in their production, largely because of reasons of ease of identification. However, the preferred polyethers of formula (I) are those wherein each r is 0 and R is phenylene, particularly para-phenylene. With the spiro ring system, polyethers where Z' is hydrogen or methyl are preferred when Z is acyclic and polyethers wherein Z" is benzo are preferred when Z is cyclic.

The polyethers are produced by reaction of (1) a [4.4] spirodilactam having nitrogen atoms in the 1- and 6-spiro ring positions and a hydroxy-aryl-containing substituent on each spiro ring nitrogen atom with (2) a [4.4] spirodilactam having nitrogen atoms in the 1- and 6-spiro ring positions and a glycidyloxyaryl substituent on each spiro ring nitrogen atom. In terms of the preferred polyethers of the above formula (I), the spirodilactam reactants are represented by the formula

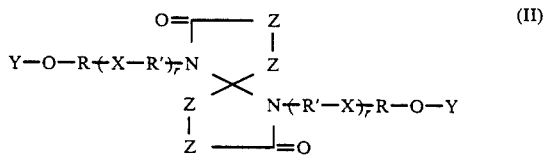

wherein R, R', r, X and Z have the previously stated meaning and Y is hydrogen or glycidyl, it being understood that one spirodilactam reactant will be of the above formula II wherein each Y is hydrogen and a second spirodilactam will be of the above formula II wherein each Y is glycidyl.

Illustrative of spirodilactam reactants having hydroxyaryl substituents (formula II, Y is hydrogen) are 1,6-di(4-hydroxyphenyl)-1,6-diazaspiro[4.4]nonane-2,7-dione; 1,6-di(3-hydroxyphenyl)-3,8-dimethyl-1,6-diazaspiro[4.4]nonane-2,7-dione; 1,6-di(4-hydroxy-3-chlorophenyl)-3,4,8,9-tetramethyl-1,6-diazaspiro-[4.4]nonane-2,7-dione; 1,6-di[4-(4-hydroxyphenyloxy)-phenyl]-1,6-diazaspiro[4.4]nonane-2,7-dione; 1,6-di[4-(3-hydroxybenzoyl) phenyl]-3,4,8,9-dibenzo-1,6-diazaspiro[4.4]nonane-2,7-dione; and 1,6-di(4-hydroxyphenyl)-3,4,8,9-dipyrido-1,6-diazaspiro[4.4]-nonane-2,7-dione. Corresponding spirodilactams having glycidyloxyaryl-containing substituents (formula (II), Y is glycidyl) include 1,6-di(4-glycidyloxyphenyl)-1,6-diazaspiro[4.4]nonane-2,7-dione; 1,6-(3-glycidyloxy-4-methylphenyl)-3,3,4,4,8,8,9,9-octamethyl-1,6-diazaspiro[4.4-]nonane-2,7-dione; 1,6-di[1-(4-glycidyloxynaphthyl)]-3,4-cyclopentano-1,6-diazaspiro[4.4]nonane-2,7-dione; 1,6-di[4-(4-glycidyloxyphenyl)phenyl]-3,4,8,9-di(cyclohexano)-1,6-diazaspiro [4.4]nonane-2,7-dione and 1,6-di(3-glycidyloxy-3,5-dibromophenyl)-1,6-diazaspiro[4.4]nonane-2,7-dione.

The hydroxyaryl-containing spirodilactam reactants are disclosed and claimed, together with methods for their production, in copending U.S. patent applications Ser. No. 172,000, filed Mar. 23, 1988, Ser. No. 172,052, filed Mar. 23, 1988 and Ser. No. 245,618, filed Sept. 16, 1988, which applications are incorporated herein by reference. The spirodilactam reactants having glycidyloxyaryl-containing substituents are disclosed and claimed in copending U.S. patent applications Ser. No. 172,054, filed Mar. 23, 1988, and Ser. No. 245,434, filed Sept. 16, 1988. Also disclosed is a method for the production thereof. These applications are incorporated herein by reference.

It will be apparent that the hydroxyaryl-containing spirodilactam reactant and the glycidyloxyaryl-containing spirodilactam reactant will combine in an equimolar ratio to produce the alternating polyhydroxy polyethers of the invention. Although a molar reactant ratio of the hydroxyaryl-containing spirodilactam reactant to the glycidyloxyaryl-containing spirodilactam reactant from about 3:1 to about 1:3 are useful in the production of the polyethers of the invention, and even higher or lower ratios may be used, the reactants are preferably employed in a molar reactant ratio that is substantially stoichiometric. It is useful in some modifications of the process of the invention to employ a polymerization catalyst which most often is a quaternary phosphonium salt. Phosphonium halides, particularly the phosphonium higher halides, i.e., the bromide or iodide, are preferred although other phosphonium salts such as the acetate or bicarbonate are also useful. The phosphonium salts are known to be useful as catalyst in this type of process and frequently are alkyltriphenylphosphonium salts. Ethyltriphenylphosphonium bromide or ethyltriphenylphosphonium iodide are particularly preferred. A phosphonium salt catalyst is not required, but when employed it is provided to the reaction mixture in catalytic quantities. Amounts of a phosphonium salt catalyst up to about 5% by weight, based on total reactants, are satisfactory.

The reaction is conducted by mixing the reactants and catalyst, if employed, and maintaining the resulting mixture under polymerization conditions. Reaction temperature should be an elevated temperature above about 150° C., preferably above about 180° C., but generally below about 300° C. Reaction pressures should be sufficient to maintain the reaction mixture in a liquid phase at reaction temperature. Substantially atmospheric pressure is generally preferred although superatmospheric pressure or slightly subatmostpheric pressures are also suitable. Reactant contact during reaction is maintained by conventional methods such as by shaking or stirring. Subsequent to reaction the product is typically recovered by conventional methods such as precipitation or selection extraction. The polyether product is often used as such without the need for further purification although the product is purified, if desired, by conventional techniques such as by dissolving the product in a suitable solvent, e.g., an ether such as tetrahydrofuran, and reprecipitating the product with a non-solvent such as methanol. The molecular weight of the polyether product will be controlled to some extent by the reaction conditions, particularly the reaction temperature. Polyether products of molecular weight from about 10,000 to about 100,000 are preferred because of the desirable properties they exhibit.

The polymeric, polyhydroxy polyethers of the invention are characterized by relatively high glass transition temperatures, typically above 150° C. or even higher. The polyethers find utility in the applications conventionally associated with phenoxy resins but are additionally useful in engineering applications such as molded containers for food and drink which are frequently exposed to elevated temperatures as during sterilization. The polyethers are processed by means of the usual techniques such as injection, compression or blow molding to produce films, shaped articles and other objects.

The invention is further illustrated by the following Illustrative Embodiments and the Comparative Example (not of the invention) which should not be construed as limiting.

ILLUSTRATIVE EMBODIMENT I

A mixture of 2.25 g (0.005 mole) of 1,6-di(4-glycidyloxyphenyl)-1,6-diazaspiro[4.4]nonane-2,7-dione, 1.69 g (0.005 mole) of 1,6-di(4-hydroxyphenyl)-1,6-diazaspiro[4.4]nonane-2,7-dione and 0.1855 g (0.0005 mole) of ethyltriphenylphosphorium bromide was placed in a reactor of 50 ml capacity equipped with a mechanical stirrer and a condenser. The reaction mixture was stirred while being warmed to 200° C. and maintained at 200° C. for 6 hours. The resulting mixture was then cooled and the polyether reaction product was isolated as a hard resin with a glass transition temperature of 167° C.

ILLUSTRATIVE EMBODIMENT II

A mixture of 1.69 g (0.05 mole) of 1,6-di(3-hydroxyphenyl)-1,6-diazaspiro[4.4]nonane-2,7-dione, 2.25 g (0.05 mole) of 1,6-di(3-glycidyloxyphenyl)-1,6-diazaspiro[4.4]nonane-2,7-dione and 0.1855 g (0.0005 mole) of ethyltriphenylphosphonium bromide was placed in a reactor of 50 ml capacity equipped with a mechanical stirrer and a condenser. The reaction mixture was stirred while being warmed to 200° C. and maintained at 200° C. for 6 hours. The resulting mixture was then cooled and the polyether reaction product was recovered as a hard resin with a glass transition temperature of 158° C.

COMPARATIVE EXAMPLE

The rection product of 2,2-di(4-glycidyloxyphenyl)propane and 2,2-di(4-hydroxyphenyl)propane was produced by the procedure of Illustrative Embodiment I. The product, a commercial resin, had a glass transition temperature of 87° C.

What is claimed is:

1. A linear, polymeric, polyhydroxy polyether having alternating moieties of (1) a [4.4] spirodilactam having spiro ring nitrogen atoms in the 1- and 6-ring positions and having an oxyaryl-containing substituent on each spiro ring nitrogen atom, and (2) a 2-hydroxy-1,3-propylene connecting group.

2. The linear, polymeric, polyhydroxy polyether of claim 1 of the repeating formula

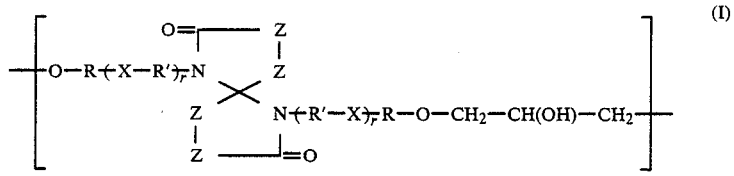

wherein Z independently is

in which Z' independently is hydrogen, lower alkyl, fluorine or chlorine, or Z is such that two adjacent Z moieties taken together form a ring system Z" of from 5 to 7 ring atoms inclusive, up to two of which are heteroatoms selected from nitrogen, oxygen or sulfur with the remainder of the ring atoms being carbon atoms, there being up to 15 carbon atoms inclusive in each Z", two of which connect a carbonyl carbon atom and the spiro carbon atom, R independently is aromatic of up to 15 carbon atoms inclusive and up to two aromatic rings, inclusive, R' independently is R or aliphatic of up to 10 carbon atoms inclusive, r independently is 0 or 1 and X independently is a direct valence bond or X independently represents alkylene of up to 8 carbon atoms inclusive, oxo, thio, sulfonyl, carbonyl, dioxyphenylene, 2,2-di(oxyphenyl)propane or dioxydiphenylene.

3. The polyether of claim 2 wherein each r is 0.

4. The polyether of claim 3 wherein Z is C(Z')$_2$ in which Z' is hydrogen or methyl.

5. The polyether of claim 3 wherein Z" is benzo.

6. The polyether of claim 3 wherein R is phenylene.

7. The polyether of claim 6 wherein the phenylene is p-phenylene.

8. A process for preparing a linear, alternating, polyhydroxy polyether by reacting, under polymerization conditions, (1) a hydroxyaryl-containing spirodilactam of the formula

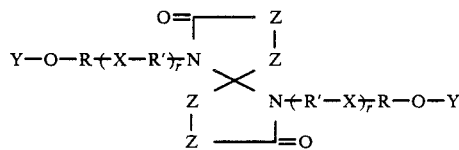

wherein Z independently is

in which Z' independently is hydrogen, lower alkyl, fluorine or chlorine, or Z is such that two adjacent Z moieties taken together form a ring system Z" of from 5 to 7 carbon atoms inclusive, up to two of which are heteroatoms selected from nitrogen, oxygen or sulfur with the remainder of the ring atoms being carbon atoms, there being up to 15 carbon atoms inclusive in each Z", two of which connect a carbonyl carbon atoms and a spiro carbon atom, R independently is aromatic of up to 15 carbon atoms and up to two aromatic rings, inclusive, R' is R or aliphatic of up to 10 carbon atoms inclusive, r is 0 or 1, X independently is a direct valence bond or X independently is alkylene of up to 8 carbon atoms inclusive, oxo, thio, sulfonyl, carbonyl, dioxyphenylene, 2,2-di(oxyphenyl)propane or dioxydiphenylene and Y is hydrogen, and (2) a glycidyloxyaryl-containing spirodilactam of the formula

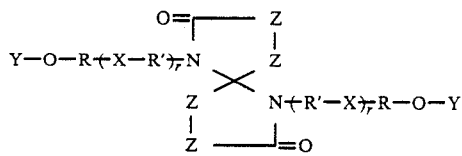

wherein R, R', r, X and Z have the previously stated meanings but Y is glycidyl.

9. The process of claim 8 wherein each r is 0.

10. The process of claim 9 wherein each R is phenylene.

11. The process of claim 10 wherein Z is C(Z')$_2$ in which Z' is hydrogen or methyl.

12. The process of claim 11 wherein R is p-phenylene.

13. The process of claim 10 wherein each Z taken together with the adjacent Z forms a ring system Z'' in which Z'' is benzo.

14. The process of claim 13 wherein R is p-phenylene.

* * * * *